United States Patent

Riedel et al.

[11] Patent Number: 6,137,013
[45] Date of Patent: Oct. 24, 2000

[54] METHOD OF STABILIZING ALDEHYDES

[75] Inventors: Michael Riedel, Bay City, Tex.; Wolfgang Zgorzelski, Oberhausen, Germany; Michael Messerschmidt, Dinslaken, Germany; Klaus Bergrath, Oberhausen, Germany

[73] Assignee: Celanese GmbH, Germany

[21] Appl. No.: 09/211,937

[22] Filed: Dec. 15, 1998

[30] Foreign Application Priority Data

Dec. 23, 1997 [DE] Germany ............ 197 57 531

[51] Int. Cl.⁷ .................................................. C07C 47/00
[52] U.S. Cl. .......................... 568/421; 568/449; 568/492
[58] Field of Search .................................. 568/421, 448, 568/449, 458, 492

[56] References Cited

U.S. PATENT DOCUMENTS 2,170,625  8/1939  Wyler ........................................ 23/250
4,020,109  4/1977  Fleck et al. ........................ 260/601 R

FOREIGN PATENT DOCUMENTS 70012282  6/1967  Japan.

OTHER PUBLICATIONS

XP–002095946, Derwent—(1 page) Section Ch, Week 8529, 1985.
SP–002095945, Chem. Abstracts, Columbus, Ohio p. 269, 1970.

*Primary Examiner*—Sreeni Padmanabhan
*Attorney, Agent, or Firm*—Bierman, Muserlian and Lucas

[57] ABSTRACT

A method of stabilizing aliphatic $C_3$–$C_{14}$-aldehydes against polymerization and autocondensation by the addition of alkaline substances to the aldehydes wherein the alkaline substances used are alkali metal hydroxides, alkaline earth metal hydroxides, alkali metal carbonates, alkaline earth metal carbonates or alkali metal carboxylates which are added to the aldehyde to be stabilized in amounts of 0.05–20 ppm, based on the aldehyde.

13 Claims, No Drawings

6,137,013

METHOD OF STABILIZING ALDEHYDES

FIELD OF THE INVENTION

A method of stabilizing aldehydes against polymerization and autocondensation.

STATE OF THE ART

Owing to their high reactivity, aldehydes have a tendency toward polymerization and autocondensation. Polymerization forms mainly trimeric products. For example, isobutyraldehyde forms 2,4,6-triisopropyl-1,3,5-trioxane, although other aliphatic aldehydes having 3–14 carbon atoms also polymerize to form the cyclic trimeric aldehyde (trialkyltrioxane). The trimerization is catalyzed by chemical substances such as chlorine or bromine, phosphorus pentoxide, sulfuric acid, hydrogen sulfide, hydrogen chloride, hydrogen fluoride, boron trifluoride, aluminum chloride or zinc chloride. In the presence of such acid compounds, the polymerization of the aldehydes commences spontaneously.

If the concentration of the acid compound is sufficiently high, this results in formation of crystalline trimeric aldehydes within a few minutes. At concentrations of up to 10 ppm. of the acid compound, trimer formation occurs somewhat more slowly over a period of a few days. In addition, low temperatures, i.e. temperatures of about 0° C. or below, or UV light promote the polymerization of the aliphatic aldehydes. A further problem is the tendency of the aldehydes to undergo the aldol condensation in the presence of alkaline substances.

Owing to their transformation into such relatively high molecular weight compounds, aldehydes cannot be stored for an indefinite period. Although the polymerization and autocondensation products of the aldehydes redissociate at relatively high temperature, their formation stands in the way of unrestricted industrial use of the aldehydes. Efforts are therefore made to prevent the formation of relatively high molecular weight products from the aldehydes. This is possible over a limited period of time by preparing and storing the aldehydes in highly pure form. However, the purification operations required for this are so complicated that they are not feasible for commercial preparation of the aldehydes.

It is known that the polymerization and autocondensation reactions can be suppressed by addition of certain substances. In practice, these substances must meet a series of requirements if the aldehyde is to be able to be employed without restriction in a wide variety of applications. Among these is the requirement that the substance concerned has to remain active over a prolonged period, even in a low concentration and also has to cause no interference in the processing of the aldehyde as a result of chemical reactions.

Stabilizers which have been described for isobutyraldehyde are, for example, mercaptobenzimidazole and 2,2-methylenedi-(4-methyl-6-tert-butylphenol). However, these stabilizers are effective for only an insufficient time. Thus, according to DE-A-29 05 267, when 100 ppm of mercaptobenzimidazole are added to isobutyraldehyde, a considerable degree of trimerization is again observed after the stabilized aldehyde has been stored for only 5 weeks.

According to another method, a solution of diphenylamine in ethanol is added to the aldehydes to prevent polymerization. However, this procedure likewise does not ensure that the polymerization is suppressed over a prolonged period of time.

It is known from DE-A-29 05 267 and DE-A 29 17 789 that isobutyraldehyde and other aliphatic aldehydes having 3–14 carbon atoms can be stabilized against polymerization and autocondensation by addition of triethanolamine or dimethylethanolamine. When using these stabilizers, good stabilization over a prolonged period can be achieved even when relatively low concentrations are employed. It is stated, for example, that 10 ppm of the ethanolamines mentioned, based on the aldehyde, can rule out the formation of high molecular weight compounds by polymerization and autocondensation, e.g. in the presence of oxygen, for a period of 30 weeks. When 20–100 ppm, based on the aldehyde, are added, the stabilizers suppress the formation of the trimer or the aldol condensation product on storage of the aldehyde without particular pre cautions for a period of about 1 year. However, these stabilizers have the disadvantage that they can be removed again from the aldehydes only with a considerable outlay in terms of distillation.

JP 45 012282 B4 likewise addresses the problem of stabilizing isobutyraldehyde against the formation of trimers where it is stated that the treatment of isobutyraldehyde with an aqueous alkali solution is completely ineffective. Stabilization can only be achieved if the alkaline substance is added to the sobutyraldehyde as a solid or in the form of a very concentrated aqueous solution; in the latter case, it is critical that the amount of water is below the saturation limit of the isobutyraldehyde. Alkaline compounds used were alkali metal compounds (carbonate salts, bicarbonate salts, silicates and fatty acid salts), alkaline earth metal compounds (oxides, hydroxides, carbonate salts, bicarbonate salts and fatty acid salts) and ammonia or ammonium carbonate. However, the amounts of alkaline compound added are very large. In the case of sodium bicarbonate, sodium carbonate, potassium carbonate, ammonium carbonate, calcium carbonate and calcium hydroxide, sodium acetate and magnesium oxide as stabilizers, 500 ppm are in each case added to the isobutyraldehyde, an amount which is regarded as small in the context of JP 45 012282 B4.

Although the use of such large amounts of the alkaline stabilizer suppresses trimer formation, problems caused by the alkali-catalyzed aldol condensation of the isobutyraldehyde which occurs to an increasing extent are unavoidable. Furthermore, the addition of the alkaline substance as a solid to relatively large amounts of aldehyde, e.g. stored in 10 tanks, is associated with the problem of completely dissolving, dispersing and uniformly distributing the alkaline substance throughout the total aldehyde volume.

OBJECTS OF THE INVENTION

It is an object of the invention to provide an improved method which makes it possible to prevent polymerization and autocondensation reactions of the aldehydes for as long as possible a time.

This and other objects and advantages of the invention will become obvious from the following detailed description.

THE INVENTION

The method of the invention achieves this object in which aliphatic $C_3$–$C_{14}$-aldehydes are stabilized by addition of alkaline substances, comprises adding alkali metal hydroxides, alkaline earth metal hydroxides, alkali metal carbonates, alkaline earth metal carbonates or alkali metal carboxylates as alkaline substances to the aldehyde to be stabilized in amounts of 0.05–20 ppm, preferably 0.05–5 ppm, more preferably 0.05–2.5 ppm, based on the aldehyde.

The process of the invention is notable for the fact that the stabilizers used are effective even in extremely low concentrations. Even 0.05 ppm of the stabilizer prevent the formation of high molecular weight compounds by polymerization or aldol condensation on storage of the aldehyde, even at low temperatures, without further precautions for a period of several weeks.

It should also be emphasized that the substances used for stabilizing the aldehydes do not interfere in the further processing of the aldehydes. If removal of the alkaline substance before further processing of the aldehydes is nevertheless desired, this can be achieved by simple distillation in which the alkaline substance remains in the distillation bottoms. It is particularly noteworthy that the stabilizers, despite the fact that they are alkaline, trigger no aldol condensation reaction in the aldehydes.

Preferred alkali metal hydroxides are sodium and potassium hydroxide, and the preferred alkaline earth metal hydroxide is calcium hydroxide. Preferred alkali metal carbonates are sodium and potassium carbonate and preferred alkaline earth metal carbonates are magnesium and calcium carbonate. As alkali metal carboxylate, particular preference is given to using sodium butyrate.

The alkaline substances are usually used a 0.01–1m, preferably 0.05–0.5M and more preferably 0.1–0.25M, aqueous solution. In particular cases, it can also prove to be advantageous to add the alkaline substances, in particular the alkali metal carboxylates and among these preferably sodium butyrate, as solids.

Examples of aldehydes which can be stabilized by the method of the invention are propanal, n- and i-butanal, n- and i-pentanal, n- and i-hexanal, n- and i-heptanal, n- and i-octanal, n- and i-nonanal, n- and i-decanal, undecanal, dodecanal, lauric aldehyde, methylnonyl aldehyde (MNA), tridecyl aldehyde and myristyl aldehyde. These aldehydes may contain up to 3% by weight, preferably from 0.5 to 2% by weight and more preferably from 0.75 to 1.25% by weight, of water.

In one embodiment of the method of the invention, the stabilizer is initially charged in the form of the aqueous solution and the aldehyde, which may likewise contain water, is added thereto. Conversely, the aqueous solution of the stabilizer can also be added to the anhydrous or water-containing aldehyde.

In the following examples, there are described several preferred embodiments to illustrate the invention. However, it is to be understood that the invention is not intended to be limited to the specific embodiments.

EXAMPLES 1–3

The sodium hydroxide used for stabilization was placed, as a 0.1M aqueous solution, in the appropriate amount in polyethylene bottles, then admixed with the appropriate amount of aldehyde and blanketed with nitrogen. The isobutyraldehyde in Examples 1 and 2 contained, initially, 2% of deionized water in each case and the n-butyralde hyde in Example 3 contain ed 1% of deionized water.

The polyethylene bottles were subsequently shaken on a rotary shaker for 20 minutes to achieve optimum mixing. In Example 2, the bottle was shaken for the entire 4 weeks of the experiment. The bottles were stored in the absence of light for the respective times of the experiments. Sampling after the various storage times was, in each case, carried out with addition of 100 ppm of triethanolamine to ensure that the respective sample remained in the same state as at the time of sampling. The samples were analyzed by means of gas chromatography and all work was carried out under nitrogen. The results are set forth in Table 1

TABLE 1

| | Trimer formation [% by weight] | | | | | | | | |
|---|---|---|---|---|---|---|---|---|---|
| | Example 1 i-Butyraldehyde | | | Example 2 i-Butyraldehyde with continual shaking | | | Example 3 n-Butyraldehyde | | |
| NaOH Days | None | 0.17 ppm | 0.5 ppm | None | 0.2 ppm | 2 ppm | None | 0.1 ppm | 0.17 ppm |
| 0 | | 0.025 | | | 0.005 | | | 0.063 | |
| 7 | 0.305 | 0.169 | 0.048 | | | | 0.125 | 0.063 | 0.063 |
| 14 | | | | 1.611 | 0.284 | 0.085 | | | |
| 28 | | | | 2.317 | 0.434 | 0.087 | | | |

EXAMPLES 4–10

The sodium hydroxide, potassium hydroxide or sodium carbonate used for stabilization was placed, at the amount indicated in Table 2 and in the form of an aqueous solution having the concentration indicated in the table into polyethylene bottles, then admixed with the appropriate amount of n-butyraldehyde and blanketed with nitrogen.

The polyethylene bottles were then shaken on a rotary shaker for 20 minutes to achieve optimum mixing. The bottles were stored in the absence of light for the respective times of the experiments. Sampling after the various storage times was in each case carried out with addition of 100 ppm of triethanolamine to ensure that the respective sample remained in the same state as at the time of sampling. The samples were analyzed by means of gas chromatography and all work is carried out under nitrogen. The results are reported in Table 2.

TABLE 2

| | | | Sampling after (h) | | |
|---|---|---|---|---|---|
| | | | Initial | 48 h | 129 h |
| Ex. | Addition | Analysis | [% by weight] | | |
| 4 | 1% of deionized water | n-$C_4$-al | 99.928 | 99.856 | 99.545 |
| | | Trim $C_4$-al K1 | <0.005 | 0.051 | 0.279 |
| | | Trim $C_4$-al K2 | <0.005 | 0.010 | 0.054 |
| | | Σ Tetramer | <0.005 | 0.009 | 0.045 |
| | | Σ Aldol | 0.002 | 0.004 | 0.004 |
| 5 | 1% of deionized water | n-$C_4$-al | 99.928 | 99.924 | 99.919 |
| | | Trim $C_4$-al K1 | <0.005 | 0.002 | 0.092 |

TABLE 2-continued

| Ex. | Addition | Analysis | Initial | 48 h | 129 h |
|---|---|---|---|---|---|
| | | | \[% by weight\] | | |
| | + 0.17 ppm of NaOH (=0.0017% strength solution) | Trim $C_4$-al K2<br>Σ Tetramer<br>Σ Aldol | <0.005<br><0.005<br>0.002 | <0.005<br><0.005<br>0.004 | <0.005<br><0.005<br>0.004 |
| 6 | 0.5% of deionized water + 0.17 ppm of NaOH (=0.0034% strength solution) | n-$C_4$-al<br>Trim $C_4$-al K1<br>Trim $C_4$-al K2<br>Σ Tetramer<br>Σ Aldol | 99.928<br><0.005<br><0.005<br><0.005<br>0.002 | 99.921<br><0.005<br><0.005<br><0.005<br>0.004 | 99.914<br><0.005<br><0.005<br><0.095<br>0.007 |
| 7 | 0.25% of deionized water + 0.17 ppm of NaOH (=0.0068% strength solution) | n-$C_4$-al<br>Trim $C_4$-al K1<br>Trim $C_4$-al K2<br>Σ Tetramer<br>Σ Aldol | 99.928<br><0.005<br><0.005<br><0.005<br>0.002 | 99.918<br>0.002<br><0.005<br><0.005<br>0.004 | 99.907<br>0.002<br><0.005<br><0.005<br>0.007 |
| 8 | 1% of deionized water + 0.17 ppm of KOH (=0.0017% strength solution) | n-$C_4$-al<br>Trim $C_4$-al K1<br>Trim $C_4$-al K2<br>Σ Tetramer<br>Σ Aldol | 99.928<br><0.005<br><0.005<br><0.005<br>0.002 | 99.923<br><0.005<br><0.005<br><0.005<br>0.004 | 99.919<br><0.005<br><0.005<br><0.005<br>0.005 |
| 9 | 1% of deionized water + 500 ppm of $Na_2CO_3$ (=4.8% strength solution) | n-$C_4$-al<br>Trim $C_4$-al K1<br>Trim $C_4$-al K2<br>Σ Tetramer<br>Σ Aldol | 99.928<br><0.005<br><0.005<br><0.005<br>0.002 | 99.888<br><0.005<br><0.005<br><0.005<br>0.039 | 99.869<br><0.005<br><0.005<br><0.005<br>0.056 |
| 10 | 1% of deionized water + 500 ppm of NaOH (=4.8% strength solution) | n-$C_4$-al<br>Trim $C_4$-al K1<br>Trim $C_4$-al K2<br>Σ Tetramer<br>Σ Aldol | 99.928<br><0.005<br><0.005<br><0.005<br>0.002 | spontaneous commencement of aldolization | |

The abbreviations used in the table have the following meanings:

| | |
|---|---|
| n-$C_4$-al | n-Butyraldehyde |
| Trim $C_4$-al K1 | 2,4,6-Tri-n-propyl-1,3,5-trioxane with eee or aaa configuration |
| Trim $C_4$-al K2 | 2,4,6-Tri-n-propyl-1,3,5-trioxane with eea or aae configuration |
| Σ Tetramer | Tetrameric polymerization product of n-butyraldehyde |
| Σ Aldol | Total of aldol condensation products |

EXAMPLES 11–14

In all of Examples 11–14, the n-butyraldehyde containing 1% by weight of water was first acidified to an acid content of 1 ppm by addition of sulfuric acid. Example 11 was a blank to which no alkaline substance was added as stabilizer. In Examples 12 and 13, 20 ppm and 10 ppm, respectively, of solid sodium butyrate were subsequently added to the n-butyraldehyde and in Example 14, 10 ppm of sodium hydroxide were subsequently added to the n-butyraldehyde. The bottle, which was blanketed with nitrogen, was subsequently shaken on a rotary shaker for 20 minutes to ensure optimum mixing. The bottles were stored in the absence of light for the respective times of the experiments. 250 ml samples from each of the bottles were taken after the different storage times in each case with addition of 100 ppm of triethanolamine to ensure that the respective sample remained in the same state as at the time of sampling. All work was carried out under nitrogen and the samples were analyzed by means of gas chromatography. The results are reported in Table 3.

TABLE 3

| Sampling after (h) | Example<br>% by weight | 11<br>Blank (with acid) | 12<br>20 ppm of Na butyrate | 13<br>10 ppm of Na butyrate | 14<br>10 ppm of NaOH (0.05 M soln.) |
|---|---|---|---|---|---|
| 24 | n-C4-al | 96.189 | 99.707 | 99.752 | 99.838 |
| | Trim.C4-al K1 | 2.873 | 0.191 | 0.154 | 0.089 |
| | Trim.C4-al K2 | 0.552 | 0.037 | 0.031 | 0.018 |
| | Σ Tetramer | 0.346 | 0.026 | 0.021 | 0.014 |
| | Σ Aldol | 0.009 | 0.006 | 0.006 | 0.010 |
| 48 | n-C4-al | 93.160 | 99.651 | 99.710 | 99.836 |
| | Trim.C4-al K1 | 5.246 | 0.224 | 0.181 | 0.089 |
| | Trim.C4-al K2 | 1.002 | 0.045 | 0.036 | 0.017 |
| | Σ Tetramer | 0.554 | 0.033 | 0.030 | 0.015 |
| | Σ Aldol | 0.008 | 0.012 | 0.010 | 0.014 |
| 72 | n-C4-al | 91.441 | 99.639 | 99.705 | 99.815 |
| | Trim.C4-al K1 | 6.642 | 0.223 | 0.171 | 0.090 |
| | Trim.C4-al K2 | 1.247 | 0.044 | 0.035 | 0.019 |
| | Σ Tetramer | 0.621 | 0.030 | 0.031 | 0.021 |
| | Σ Aldol | 0.013 | 0.017 | 0.013 | 0.016 |
| 120 | n-C4-al | 86.996 | 99.653 | 99.717 | 99.816 |
| | Trim.C4-al K1 | 10.296 | 0.213 | 0.173 | 0.096 |
| | Trim.C4-al K2 | 1.877 | 0.042 | 0.033 | 0.018 |
| | Σ Tetramer | 0.778 | 0.027 | 0.023 | 0.014 |
| | Σ Aldol | 0.017 | 0.021 | 0.014 | 0.018 |

EXAMPLES 15–18

Example 15 was a blank to which no alkaline substance was added as stabilizer. In Examples 16, 17 and 18, 0.5 ppm of solid sodium butyrate, solid calcium butyrate and sodium hydroxide were subsequently added as a 0.05M solution to the n-butyraldehyde. The bottle, which was blanketed with nitrogen, was subsequently shaken on a rotary shaker for 20 minutes to ensure optimum mixing. The bottles were stored in the absence of light for the respective times of the experiments. 250 ml samples from each of the bottles were taken after the different storage times in each case with addition of 100 ppm of triethanolamine to ensure that the respective sample remained in the same state as at the time of sampling. All work was carried out under nitrogen and the samples were analyzed by means of gas chromatography. The results are reported in Table 4.

EXAMPLES 19–21

Example 19 was a blank to which no alkaline substance was added as stabilizer. In Examples 20 and 21, 0.5 ppm and 0.25 ppm, respectively, of sodium hydroxide were subsequently added as a 0.1M solution to the n-butyraldehyde. The bottle, which was blanketed with nitrogen, was subsequently shaken on a rotary shaker for 20 minutes to ensure optimum mixing. The bottles were stored in the absence of light for the respective times of the experiments. 250 ml samples from each of the bottles were taken after the different storage times in each case with addition of 100 ppm of triethanolamine to ensure that the respective sample remained in the same state as at the time of sampling. All work was carried out under nitrogen and the samples were analyzed by means of gas chromatography. The results are reported in Table 5.

TABLE 4

| Sampling after (h) | Example % by weight | 15 Blank | 16 0.5 ppm of Na butyrate/solid | 17 0.5 ppm of Ca butyrate/solid | 18 0.5 ppm of NaOH (0.05 M soln.) |
|---|---|---|---|---|---|
| 24 | n-C4-al | 99.886 | 99.950 | 99.899 | 99.946 |
|  | Trim.C4-al K1 | 0.040 | <0.005 | 0.031 | <0.005 |
|  | Trim.C4-al K2 | 0.008 | <0.005 | 0.006 | <0.005 |
|  | Σ Tetramer | 0.005 | <0.005 | 0.004 | <0.005 |
|  | Σ Aldol | 0.006 | 0.004 | 0.006 | 0.006 |
| 72 | n-C4-al | 99.802 | 99.939 | 99.888 | 99.934 |
|  | Trim.C4-al K1 | 0.097 | <0.005 | 0.033 | 0.002 |
|  | Trim.C4-al K2 | 0.019 | <0.005 | 0.007 | <0.005 |
|  | Σ Tetramer | 0.014 | <0.005 | 0.003 | <0.005 |
|  | Σ Aldol | 0.006 | 0.008 | 0.006 | 0.008 |
| 120 | n-C4-al | 99.652 | 99.944 | 99.897 | 99.940 |
|  | Trim.C4-al K1 | 0.212 | <0.005 | 0.031 | <0.005 |
|  | Trim.C4-al K2 | 0.040 | <0.005 | 0.006 | <0.005 |
|  | Σ Tetramer | 0.030 | <0.005 | 0.003 | <0.005 |
|  | Σ Aldol | 0.005 | 0.007 | 0.006 | 0.007 |

TABLE 5

| Sampling after (h) | Example % by weight | 19 Blank | 20 0.5 ppm of NaOH (0.1 M solution) | 21 0.25 ppm of NaOH (0.1 M solution) |
|---|---|---|---|---|
| 24 | n-C4-al | 99.633 | 99.954 | 99.907 |
|  | Trim.C4-al K1 | 0.241 | 0.006 | 0.035 |
|  | Trim.C4-al K2 | 0.46 | <0.005 | 0.007 |
|  | Σ Tetramer | 0.032 | <0.005 | <0.005 |
|  | Σ Aldol | 0.004 | 0.006 | 0.005 |
| 72 | n-C4-al | 99.023 | 99.951 | 99.899 |
|  | Trim.C4-al K1 | 0.696 | 0.005 | 0.036 |
|  | Trim.C4-al K2 | 0.132 | <0.005 | 0.007 |
|  | Σ Tetramer | 0.096 | <0.005 | 0.004 |
|  | Σ Aldol | 0.006 | 0.008 | 0.007 |
| 96 | n-C4-al | 98.815 | 99.953 | 99.913 |
|  | Trim.C4-al K1 | 0.871 | 0.004 | 0.030 |
|  | Trim.C4-al K2 | 0.165 | <0.005 | 0.006 |
|  | Σ Tetramer | 0.110 | <0.005 | 0.004 |
|  | Σ Aldol | <0.005 | 0.008 | 0.005 |

Various modifications of the process of the invention may be made without departing from the spirit or scope thereof and it should be understood that the invention is intended to be limited only as defined in the appended claims.

What we claim is:

1. A method of stabilizing aliphatic aldehydes of 3 to 14 carbon atoms by addition of alkaline substances, comprising adding a member of the group consisting of alkali metal hydroxides, alkaline earth metal hydroxides, alkali metal carbonates, alkaline earth metal carbonates and alkali metal carboxylates as alkaline substances to the aldehyde to be stabilized in amounts of 0.05–20 ppm, based on the aldehyde.

2. The method of claim 1, wherein the alkaline substance is selected from the group consisting of sodium hydroxide, potassium hydroxide, calcium hydroxide, sodium carbonate, potassium carbonate, magnesium carbonate, calcium carbonate and sodium butyrate.

3. The method of claim 1, wherein the alkaline substance is used as a 0.01–1M, aqueous solution.

4. The method of claim 1, wherein the aliphatic aldehyde is selected from the group consisting of propanal, n- and i-butanal, n- and i-pentanal, n- and i-hexanal, n- and i-heptanal, n- and i-octanal, n- and i-nonanal, n- and i-decanal, undecanal, dodecanal, lauric aldehyde, methylnonyl aldehyde (MNA), tridecyl aldehyde and myristyl aldehyde.

5. The method of claim 4, wherein the aldehydes contain up to 3% by weight, of water.

6. The method of claim 1, wherein the alkaline substance is initially charged in the form of an aqueous solution and the aldehyde, which may likewise contain water, is added thereto.

7. The method of claim 1, wherein the aqueous solution of the alkaline substance is added to the anhydrous or water-containing aldehyde.

8. The method of claim 1, wherein the amount of alkaline substance is 0.05 to 5 ppm by weight.

9. The method of claim 1, wherein the amount of alkaline substance is 2.5 to 5 ppm by weight.

10. The method of claim 3, wherein the alkaline substance is used as a 0.05 to 0.5M, aqueous solution.

11. The method of claim 3, wherein the alkaline substance is used as a 0.1 to 0.25M, aqueous solution.

12. The method of claim 5 wherein the aldehyde contains 0.5 to 2% by weight of water.

13. The method of claim 5 wherein the aldehyde contains 0.75 to 1.25% by weight of water.

* * * * *